(12) United States Patent
Weng

(10) Patent No.: US 12,171,950 B2
(45) Date of Patent: Dec. 24, 2024

(54) MUSIC MATCHING APPLICATION SYSTEM WITH USE OF ADVANCED GLYCATION END-PRODUCTS AND METHOD THEREOF

(71) Applicant: NATIONAL CHENG KUNG UNIVERSITY, Tainan (TW)

(72) Inventor: Chen-Hsun Weng, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 763 days.

(21) Appl. No.: 17/482,629

(22) Filed: Sep. 23, 2021

(65) Prior Publication Data

US 2022/0096786 A1    Mar. 31, 2022

Related U.S. Application Data

(60) Provisional application No. 63/083,863, filed on Sep. 26, 2020.

(51) Int. Cl.
*A61M 21/00*  (2006.01)
*G16H 20/70*  (2018.01)
*G16H 40/67*  (2018.01)

(52) U.S. Cl.
CPC ............ *A61M 21/00* (2013.01); *G16H 20/70* (2018.01); *G16H 40/67* (2018.01); *A61M 2021/0027* (2013.01); *A61M 2209/088* (2013.01); *A61M 2230/201* (2013.01)

(58) Field of Classification Search
None
See application file for complete search history.

(56) References Cited

U.S. PATENT DOCUMENTS

| | | | | |
|---|---|---|---|---|
| 8,911,989 | B2 * | 12/2014 | Lee | B01F 33/30 |
| | | | | 435/303.1 |
| 10,485,457 | B2 * | 11/2019 | Farooqui | A61B 5/14532 |
| 2005/0272001 | A1 * | 12/2005 | Blain | A61C 1/0084 |
| | | | | 601/162 |
| 2017/0326170 | A1 * | 11/2017 | Lee | A61P 39/02 |
| 2018/0256085 | A1 * | 9/2018 | Farooqui | A61B 5/4839 |
| 2020/0297574 | A1 * | 9/2020 | Poon | A61H 31/005 |
| 2024/0307336 | A1 * | 9/2024 | Venn-Watson | A61K 31/205 |

* cited by examiner

Primary Examiner — LaToya M Louis
(74) Attorney, Agent, or Firm — WPAT, P.C

(57) ABSTRACT

A music matching application system with use of AGEs and a method thereof, using a sensor unit of a wearable device to detect a first parameter value of a skin surface, followed by using a computation processing unit to perform computation process based on the first parameter value in order to obtain an electric signal and to convert into a corresponding concentration value of the AGEs. In addition, a music unit is driven to correspondingly play one of the first music menus according to the concentration value, and different music program can be provided according to the concentration level, and a second music menu is further played according to a concentration change amount corresponding to a time interval. Consequently, the effect of the music program can be enhanced.

10 Claims, 3 Drawing Sheets

MUSIC MATCHING APPLICATION SYSTEM WITH USE OF ADVANCED GLYCATION END-PRODUCTS AND METHOD THEREOF

CROSS REFERENCE

The non-provisional application claims the benefit of American Provisional Application No. 63/083,863, filed on Sep. 26, 2020, the contents thereof are incorporated by reference herein.

BACKGROUND OF THE INVENTION

1. Technical Field

The present invention relates to a music matching system and a method thereof, and in particular, to a music matching application system with use of Advanced Glycation End-Products (AGEs) and a method thereof.

2. Description of Related Technology

Alzheimer's disease refers to the condition where the degeneration rate of brain nerve cells is faster than the normal condition such that the normal operational function can be lost, leading to cognitive impairment. According to researches, the comparison between the protein in the brain frontal lobe of a patient with Alzheimer's disease and that of a healthy senior person, the Advanced Glycation End-Products (AGEs) of the protein of such patient is three times higher than that of the healthy senior person. In addition, according to mouse experiments, the result also indicates that AGEs can be toxic to cranial nerves. In other words, AGEs can be lethal to human brains. Nevertheless, if the glycation of brain can be suppressed, then there is a great chance that the incidence of Alzheimer's disease can be reduced. All of such findings explain the importance of the AGEs indicator.

Regarding the common treatments and methods adopted to delay the dementia, these methods mostly include non-drug therapies of cognitive training, reminiscence therapy, phototherapy, massage therapy, music therapy, aromatherapy, pet therapy and art therapy, adopted to improve or delay the dementia. However, in general, the therapeutic effect of known non-drug therapies cannot be tracked in real-time such that its curative effect cannot be known. Furthermore, such therapies typically require the caregiver to accompany with the patient to proceed to the treatment related place for the course of treatment. As a result, the patient's will to receive treatment may be reduced or patient may not be able to receive the treatment due to reason of the time limitation of the caregiver, etc.

The present invention provides a music matching application system with use of Advanced Glycation End-Products (AGEs) and a method thereof, such that an automatic sensor unit can be installed on a wearable device to detect the skin surface of a patient and to perform further computation process, in order to obtain the concentration value of AGEs of the patient. In addition, different music program can be provided according to the concentration, such that during the playing the music program, the concentration value can be further detected again to determine whether such value decreases. Furthermore, the music program can also be revised in real-time according to the change of the concentration value. As a result, the effect of the music program can be achieved at any time, and it can be implemented easily at home environment, such that its convenience can be significantly increased.

BRIEF SUMMARY OF THE INVENTION

The primary objective of the present invention is to provide a music matching application system with use of AGEs, capable of using a sensor unit of a wearable device to detect a first parameter value of a skin surface, followed by using a computation processing unit to perform computation process based on the first parameter value in order to obtain an electric signal and to convert into a corresponding concentration value of the AGEs, following which a music unit is driven to correspondingly play one of the first music menus according to the concentration value, and a second music menu is further played according to a concentration change amount corresponding to a time interval. Consequently, it is able to achieve the effect of significant improvement of the music program and the effect of confirming the music program provided in real-time, thereby further correcting the music program used.

Another objective of the present invention is to provide a music matching application method with use of AGEs, and the steps include the computation processing unit driving the music unit to correspondingly play one of the first music menus according to the concentration value, in order to provide a music program of different level according to the concentration value of AGEs of the patient. In addition, after the music program is received, if its effect is less than expectation, the computation processing unit then correspondingly plays the second music menu according to the concentration change amount. Consequently, in addition to the original music program, it further includes stimulation sound, thereby enhancing the effect of the music program.

To achieve the aforementioned objective, the present invention provides a music matching application system with use of Advanced Glycation End-Products (AGEs), comprising: a wearable device, comprising a wearable piece and sensor unit; the sensor unit arranged on the wearable piece; the wearable piece configured to be worn by a skin surface of a human body; and the sensor unit configured to detect a first parameter value of the skin surface during a first time; a computation processing unit connected in signal with the sensor unit to receive the first parameter value and to perform computation process, in order to obtain a first electric signal; and a music unit connected in signal with the computation processing unit and comprising a plurality of first music menus and a second music menu;

wherein the computation processing unit performs computation process based on the first electric signal to generate a first concentration value corresponding to AGEs, and performs computation process based on the first concentration value to generate a first matching result; the computation processing unit drives the sensor unit to detect a second parameter value of the skin surface during a second time; the computation processing unit receives the second parameter value to perform computation process in order to obtain a second electric signal; the computation processing unit performs computation process based on the second electric signal to generate a second concentration value corresponding to the AGEs; the computation processing unit generates a concentration change amount based on a difference between the first concentration value and the second concentration value; when the concentration change amount is not less than a predefined concentration change amount, a second matching result is generated, or when the concentration change amount is less than the predefined concentration change amount, a third matching result is generated; wherein the first matching result refers to the computation processing unit driving the music unit to play one of the plurality of first music menus correspondingly according to the first concentration value;

wherein the second matching result refers to the computation processing unit driving the music unit to play one of the plurality of first music menus correspondingly according to the second concentration value;

wherein the third matching result refers to the computation processing unit driving the music unit to play one of the plurality of first music menus correspondingly according to the second concentration value, and driving the music unit to play the second music menu according to the concentration change amount during a corresponding time interval.

In a preferred embodiment, the sensor unit is a capacitive bio-sensor, an optical bio-sensor or an ultrasonic bio-sensor.

In a preferred embodiment, the predefined concentration value comprises a first predefined concentration range, a second predefined concentration range and a third predefined concentration range; the first predefined concentration range is less than 300 mg/dL; the second predefined concentration rang is between 300 mg/dL and 600 mg/dL; and the third predefined concentration range is greater than 600 mg/dL.

In a preferred embodiment, the first matching result comprises a first time information, allowing the music unit to play one of the plurality of first music menus correspondingly according to the first time information.

In a preferred embodiment, the second matching result comprises a second time information, allowing the music unit to play one of the plurality of first music menus correspondingly according to the second time information.

In a preferred embodiment, the third matching result comprises a third time information, allowing the music unit to play one of the plurality of first music menus correspondingly according to the third time information.

In a preferred embodiment, the music unit comprises a third music menu; when the first concentration value falls within the third predefined concentration range, the computation processing unit drives the music unit to play the third music menu.

In a preferred embodiment, the predefined concentration change amount is between 10 mg/dL and 30 mg/dL.

In a preferred embodiment, the time interval comprises a first time interval, a second time interval and a third time interval.

In a preferred embodiment, when the concentration change amount is less than 10 mg/dL, it corresponds to the first time interval; when the concentration change amount is not less than 10 mg/dL but less than 20 mg/dL, it corresponds to the second time interval; and when the concentration change amount is not less than 20 mg/dL but less than 30 mg/dL, it corresponds to the third time interval.

To achieve another aforementioned objective, the present invention provides a music matching application method with use of Advanced Glycation End-Products (AGEs), comprising the steps of: a sensor unit of a wearable device detecting a first parameter value of a skin surface during a first time; a computation processing unit receiving the first parameter value and performing computation process based on the first parameter value to obtain a first electric signal; the computation processing unit performing computation process based on the first electric signal to generate a first concentration value corresponding to AGEs; the computation processing unit performing computation process based on the first concentration value to generate a first matching result; the computation processing unit driving the sensor unit to detect a second parameter value of the skin surface during a second time; the computation processing unit receiving the second parameter value and performing computation process based on the second parameter value to obtain a second electric signal; the computation processing unit performing computation process based on the second electric signal to generate a second concentration value corresponding to the AGEs; the computation processing unit generating a concentration change amount based on a difference between the first concentration value and the second concentration value; and when the concentration change amount being not less than a predefined concentration change amount, generating a second matching result, or when the concentration change amount being less than the predefined concentration change amount, generating a third matching result;

wherein the first matching result refers to the computation processing unit driving the music unit to play one of the plurality of first music menus correspondingly according to the second concentration value;

wherein the second matching result refers to the computation processing unit driving the music unit to play one of the plurality of first music menus correspondingly according to the second concentration value;

wherein the third matching result refers to the computation processing unit driving the music unit to play one of the plurality of first music menus correspondingly according to the second concentration value, and driving the music unit to play a second music menu according to the concentration change amount during a corresponding time interval.

In a preferred embodiment, the sensor unit is a capacitive bio-sensor, an optical bio-sensor or an ultrasonic bio-sensor.

In a preferred embodiment, the predefined concentration value comprises a first predefined concentration range, a second predefined concentration range and a third predefined concentration range; the first predefined concentration range is less than 300 mg/dL; the second predefined concentration rang is between 300 mg/dL and 600 mg/dL; and the third predefined concentration range is greater than 600 mg/dL.

In a preferred embodiment, the first matching result comprises a first time information, allowing the music unit to play one of the plurality of first music menus correspondingly according to the first time information.

In a preferred embodiment, the second matching result comprises a second time information, allowing the music unit to play one of the plurality of first music menus correspondingly according to the second time information.

In a preferred embodiment, the third matching result comprises a third time information, allowing the music unit to play one of the plurality of first music menus correspondingly according to the third time information.

In a preferred embodiment, the music unit comprises a third music menu; when the first concentration value falls within the third predefined concentration range, the computation processing unit drives the music unit to play the third music menu.

In a preferred embodiment, the predefined concentration change amount is between 10 mg/dL and 30 mg/dL.

In a preferred embodiment, the time interval comprises a first time interval, a second time interval and a third time interval.

In a preferred embodiment, when the concentration change amount is less than 10 mg/dL, it corresponds to the first time interval; when the concentration change amount is not less than 10 mg/dL but less than 20 mg/dL, it corresponds to the second time interval; and when the concentration change amount is not less than 20 mg/dL but less than 30 mg/dL, it corresponds to the third time interval.

The advantageous effect of the present invention refers to that the sensor unit installed on the wearable device can be used to detect the skin surface, and computation processing unit is able to perform computation process in order to generate a corresponding AGEs concentration value, following which the music unit can be driven to correspondingly play one of the first music menus according to the concentration value, and a second music menu can be further played according to the concentration change amount corresponding to the time interval. Consequently, it is able to achieve the effect of confirmation of the music program and to further correct the music solution, thereby significantly increasing the effect of music program.

DETAILED DESCRIPTION OF THE INVENTION

Please refer to the following detailed description of the preferred embodiments of the present invention in conjunction with the accompanied drawings for relevant claimed features and technical content of the present invention.

Figure 1:
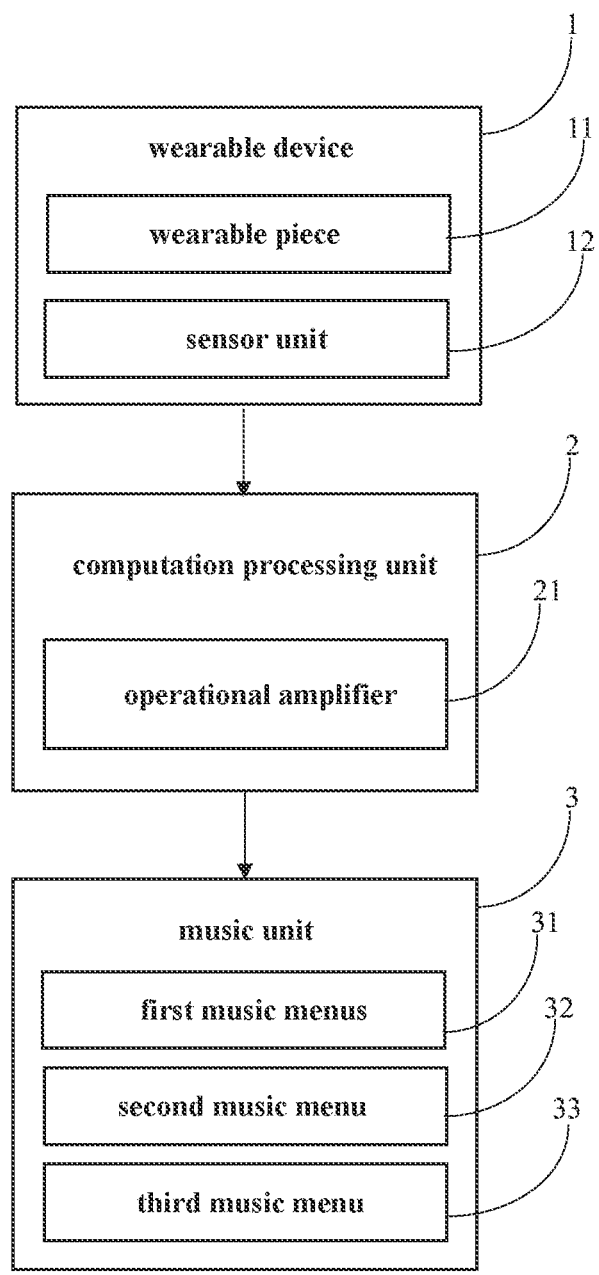
FIG. 1 is a schematic view of the system according to an embodiment of the present invention.
Figure 2:
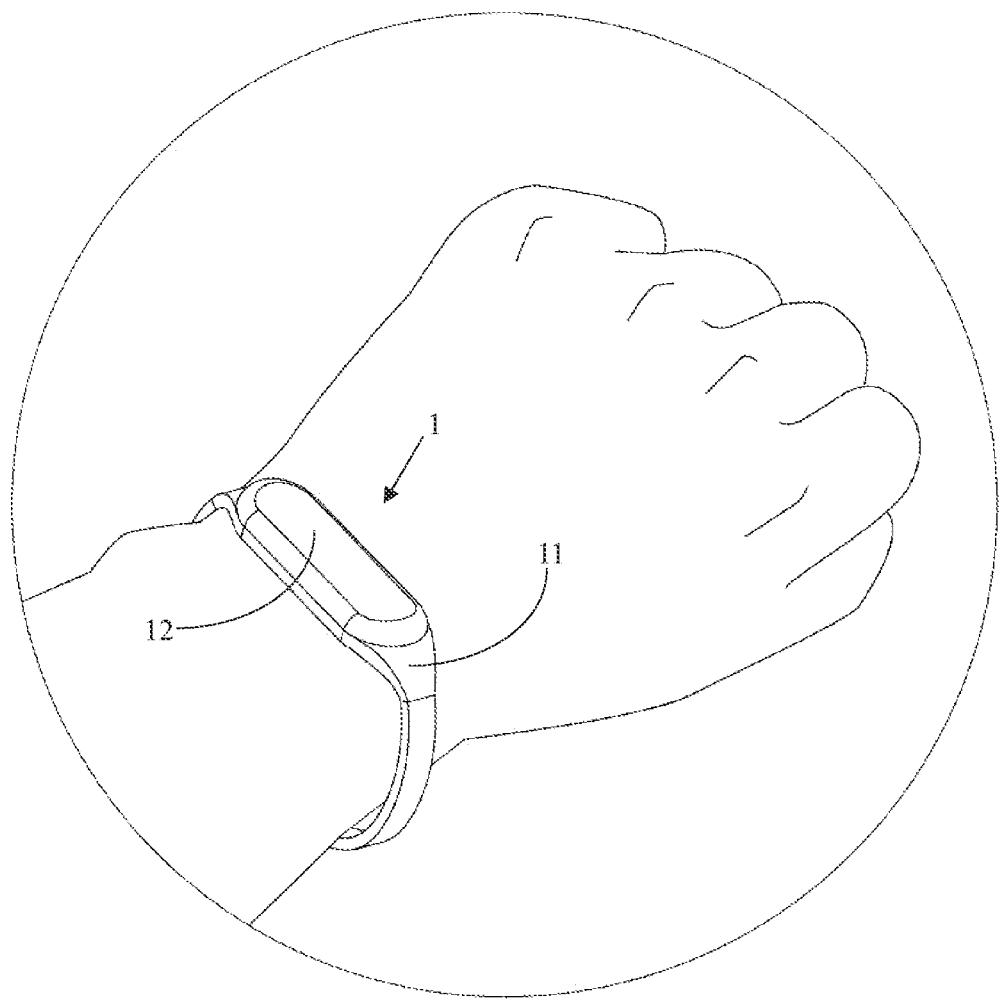
FIG. 2 is a wearing schematic view according to an embodiment of the present invention.

Please refer to FIG. 1 and FIG. 2, showing a schematic view of the system and a wearing schematic view according to an embodiment of the present invention respectively. As shown in the drawings, a music matching application system with use of Advanced Glycation End-Products (AGEs) of the present invention comprises a wearable device 1, a computation processing unit 2 and a music unit 3. The wearable device 1 comprises a wearable piece 11 and a sensor unit 12. The computation processing unit 2 is connected in signal with the music unit 3 and the sensor unit 12 of the wearable device 1 respectively. The actuation method of this system is explained in detail as follows:

The wearable device 1 comprises the wearable piece 11 and the sensor unit 12. The sensor unit 12 is arranged on the wearable piece 11. In addition, in this embodiment, the wearable piece 11 is in the form of a watch for wearing on the limb, or it can be in the form of a patch for attaching onto the skin surface of a human body; however, the present invention is not limited to such forms and types only.

The sensor unit 12 is a non-invasive sensor unit, such as a capacitive bio-sensor, an optical bio-sensor or an ultrasonic bio-sensor; however, the present invention is not limited to such types only, and the parameters can be different depending upon different type of sensors. In this embodiment, when the sensor unit 12 is a capacitive bio-sensor, the sensor unit 12 detects the parameter value, i.e. the body fluid information, of the skin surface, and the computation processing unit 2 receives the parameter value and obtains an electric signal based on the parameter value. In another embodiment, the sensor unit 12 is an optical bio-sensor, and a light source is emitted. After the light source reaches the skin surface, the human blood is able to absorb specific light source wavelength, such that the sensor unit 12 is able to detect the parameter value, i.e. the reflected light, of the skin surface, and the computation processing unit 2 receives the parameter value and obtains an electric signal based on the parameter value. In still another embodiment, the sensor unit 12 is an ultrasonic bio-sensor, and it is able to convert an electrical energy into ultrasonic wave, such that when it contacts tissue interface of different density, the sensor unit 12 is able to detect the parameter value, i.e. the reflected sonic energy, of the skin surface, and the computation processing unit 2 receives the parameter value and obtains an electric signal based on the parameter value. However, the present invention is not limited to such configurations and types only.

The computation processing unit 2 comprises an operational amplifier 21. The operational amplifier 21 is an analogue circuit module, which uses differential voltage input and generates single voltage output, and it is classified into four types of models. The first type is the voltage amplifier with both voltage input and output; the second type is the current amplifier with both current input and output; the third type is the transconductance amplifier capable of converting voltage input into current output; and the fourth type is the transimpedance amplifier capable of converting current input into voltage output. However, the present invention is not limited to such types only. After the computation processing unit 2 receives the electric signal of the sensor unit 12, the operational amplifier 21 amplifies the electric signal, following which the computation processing unit 2 then performs processing according to the electric signal and generates a corresponding concentration value of AGEs.

In this embodiment, the music unit 3 can be a computer or a multimedia playing device; however, the present invention is not limited to such types only. In addition, the music unit 3 comprises a plurality of first music menus 31, a second music menu 32 and a third music menu 33. The plurality of first music menus 31 comprises a plurality of music, including favorite songs of the patient or other rhythms or songs familiar to the patient. In this embodiment, the plurality of music can be classified into classic song type, classic rhythm type and light music type. Since most patients with dementia are able to recall past occurrences clearly but cannot remember recent events, the classic song type mainly refers to songs that the patient used to listen to when he or she was young, such as, lyrics capable of guiding the memory of the patient and assisting the patient to recall the meaning of lyrics or past occurrences. The classic rhythms mainly refer to the rhythms occurred frequently during the past era of the patient, such as percussion music played during festival events, in order to guide the patient to recall pleasant festival memories in the past through humming or singing. The light music type mainly refers to bird chirping sounds, and piano music, etc., in order to guide the patient to relaxation. Accordingly, in this embodiment, the cognition level of the music type guidance can be generally classified as guided cognition level of the classic song type greater than the guided cognition level of the classic rhythm type, and the guided cognition level of the classic rhythm type is greater than the guided cognition level of the light music type. However, the present invention is not limited to such configurations and types only.

In this embodiment, the first music menus 31 may comprise Music Menu A, Music Menu B and Music Menu C, and its design may be as follows; however, the present invention is not limited to the following configurations and types only.

Music Menu A consists of 6 light music, 4 classic rhythms and 2 classic songs; Music Menu B consists of 4 light music, 6 classic rhythms and 2 classic songs; and Music Menu C consists of 2 light music, 4 classic rhythms and 6 classic songs.

Accordingly, Music Menu A is mainly to achieve relaxation for the patient, such that it focuses more on the light music. For Music Menu B, it is mainly to achieve the gradual guidance of the cognition level of the patient, such that it focuses more on the classic rhythms Finally, for Music Menu C, it is mainly to enhance the cognition level of the patient, such that it focuses more on the classic songs. However, the present invention is not limited to such configurations and types only.

The second music menu 32 also consists of a plurality of music, and such music may be rhythms or songs that the patient dislikes or fears. In this embodiment, such music may be thunder rumbling sound, lion roaring sound, gun fire sound, Styrofoam rubbing sound, and fingernail board scratching sound, etc. However, the present invention is not limited to such types only. The purpose of such music is to promote the short-term increase of the norepinephrine through music stimulation, thereby increasing the mental ability and achieving long-term effect on the dementia treatment. According to the past researches, the accumulation of amyloid on neurons can cause Alzheimer's disease; and if the damaged neurons of the patient are immersed in norepinephrine, the condition of damaged neurons can be improved. In view of such result, the second music menu 32 is included as part of the music program, thereby achieving more prominent outcome of the music program.

The third music menu 33 mainly consists of a plurality of recordings. In this embodiment, the recording content may include greeting, self-introduction, or reading of newspaper and magazines from the family members or main caregivers of the patient. However, the present invention is not limited to such types only. The main propose of such method is to enhance the reality orientation of patients with dementia such that through the calling of the patient's name during greeting and self-introduction of family members, the patient can be guided to recall and to think subjects of various aspects of people, event, time, place and object, etc. in the reality. In addition, the reading of newspaper or magazines is able to guide the patient to understand the current events, thereby further enhancing the cognition level of the patient.

Figure 3:
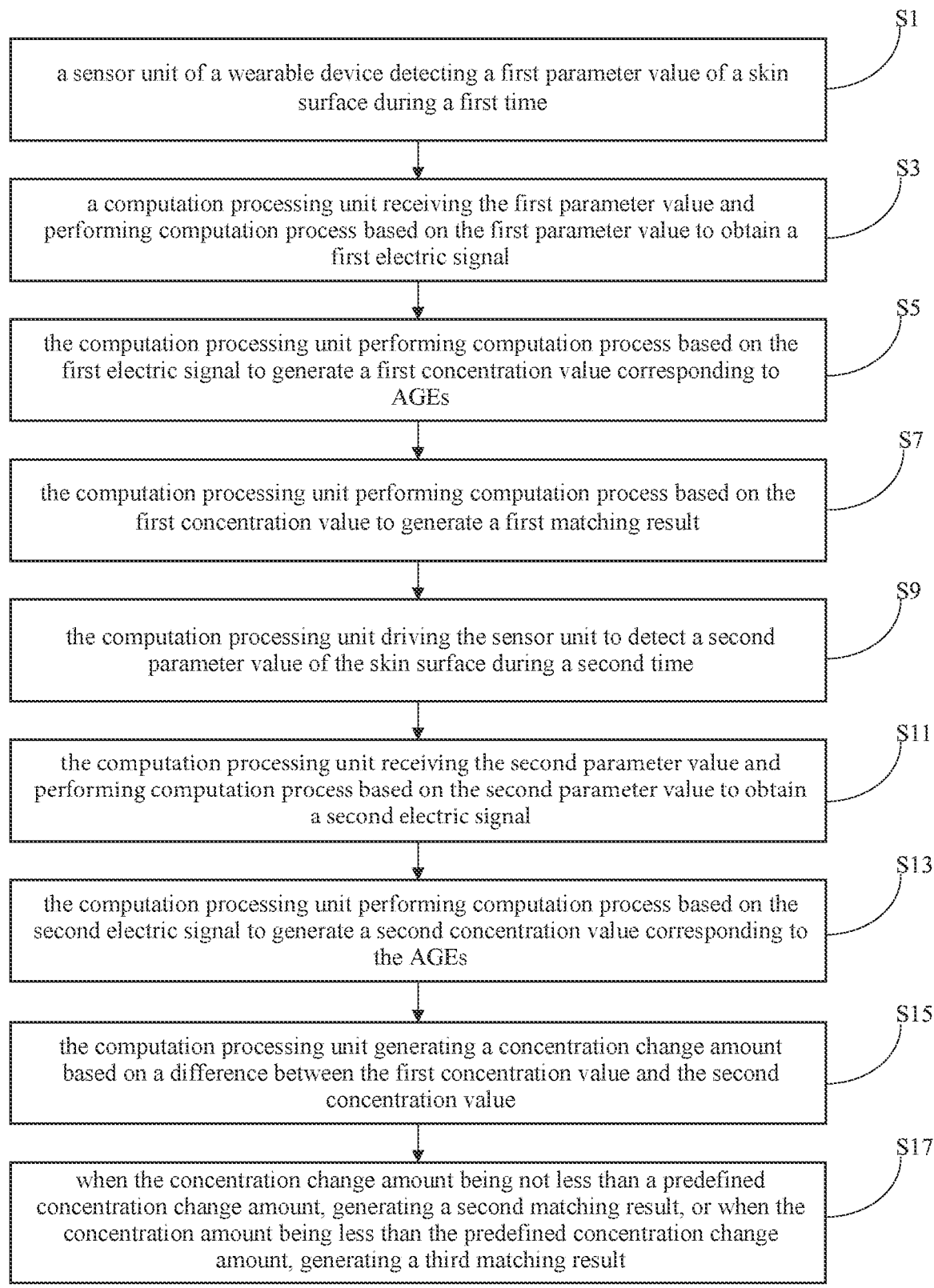
FIG. 3 is a flow chart of the method according to an embodiment of the present invention.

To further illustrate the actuation process of the present invention, please refer to FIG. 3 showing a flow chart of the method according to an embodiment of the present invention. As show in the drawing, the present invention provides a music matching application system with use of Advanced Glycation End-Products (AGEs), comprising the following steps:

Step S1: a sensor unit of a wearable device detecting a first parameter value of a skin surface during a first time;

Step S3: a computation processing unit receiving the first parameter value and performing computation process based on the first parameter value to obtain a first electric signal;

Step S5: the computation processing unit performing computation process based on the first electric signal to generate a first concentration value corresponding to AGEs;

Step S7: the computation processing unit performing computation process based on the first concentration value to generate a first matching result;

Step S9: the computation processing unit driving the sensor unit to detect a second parameter value of the skin surface during a second time;

Step S11: the computation processing unit receiving the second parameter value and performing computation process based on the second parameter value to obtain a second electric signal;

Step S13: the computation processing unit performing computation process based on the second electric signal to generate a second concentration value corresponding to the AGEs;

Step S15: the computation processing unit generating a concentration change amount based on a difference between the first concentration value and the second concentration value; and Step S17: when the concentration change amount being not less than a predefined concentration change amount, generating a second matching result, or when the concentration amount being less than the predefined concentration change amount, generating a third matching result.

As shown in Step S1, the wearable device 1 can be worn on a skin surface of a human body with the wearable piece 11, and the sensor unit 12 can be used to detect the first parameter value of the skin surface. In this embodiment, the sensor unit 12 uses a capacitive bio-sensor as an example for illustration, and first parameter value of the skin surface detected by the sensor unit 12 refers to the body fluid information; however, the present invention is not limited to such types only.

As shown in Step S3, the computation processing unit 2 receives the first parameter value and obtains the first electric signal based on the first parameter value, following which in Step S5, the first electric signal is amplified by the operational amplifier 21 and is further processed by the computation processing unit 2, in order to generate the first concentration value corresponding to AGEs.

As shown in Step S7, the computation processing unit 2 performs computation process based on the first concentration value in order to generate the first matching result. The first matching result refers to that when the computation processing unit 2 determines which interval the first concentration value belongs to, it then plays one of the plurality first music menus 31 correspondingly.

In this embodiment, the predefined concentration value is classified into three types of ranges, meaning that the predefined concentration value comprises a first predefined concentration range, a second predefined concentration range and a third predefined concentration range, and their ranges respectively refers to as less than 300 mg/dL, between 300 mg/dL and 600 mg/DL, and greater than 600 mg/dL. In other words, when the concentration range of the AGEs is less than 300 mg/dL, it then infers that there is an increasing risk of the tendency of cognitive impairment; when the concentration range of the AGEs is between 300 mg/dL and 600 mg/dL, it then infers that there is an increasing risk of cognitive impairment; when the concentration range of the AGEs is greater than 600 mg/dL, it then infers that cognitive impairment has occurred. However, the present invention is not limited to such configurations and types only.

In this embodiment, the plurality of first music menus 31 are classified into three types of music menus, i.e. Music Menu A, Music Menu B and Music Menu C; however, the present invention is not limited to such types only. Accordingly, when the first concentration value falls within the first predefined concentration range, it then plays the Music Menu A correspondingly; or when the first concentration value falls within the second predefined concentration range, it then plays the Music Menu B correspondingly; or when the first concentration value falls within the third predefined concentration range, it then plays the Music Menu C correspondingly. However, the present invention is not limited to such configurations and types only; for example, additionally, when the first concentration value falls within the third predefined concentration range, at this time, the computation processing unit 2 drives the music unit 3 to play the first music menus 31 and the third music menu 33 in turns.

In addition, the first matching result comprises a first time information, allowing the music unit 3 to play one of the plurality of first music menus according to the first time information. In this embodiment, Music Menu A is used as an example for illustration, and its time allocation is as follows: Three light musics are played at 5:30, two classic rhythms are played at 11:30, two classic songs are played at 14:30, two classic rhythms are played at 17:30 and three light musics are played at 21:30. For Music Menu B, as an example for illustration, its time allocation is as follows: Two light musics are played at 5:30, three classic rhythms are played at 11:30, two classic songs are played at 14:30, three classic rhythms are played at 17:30 and two light musics are played at 21:30. For Music Menu C, as an example for illustration, its time allocation is as follows: One light music and two classic rhythms are played at 5:30, two classic songs are played at 11:30, two classic songs are played at 14:30, two classic songs are played at 17:30 and one light music and two classic rhythms are played at 21:30. Accordingly, it is able to assist the patient to establish a daily routine while assisting the patient to improve emotional state and to promote thinking at the same time.

As shown in Step S9, the computation processing unit 2 drives the sensor unit 2 to detect a second parameter value during a second time. Then, in Step S11, the computation processing unit 2 performs computation process based on the second parameter and obtains a second electric signal. Since the method is similar to that of Steps S1~S3, details thereof are omitted hereafter. In addition, the first time is earlier than the second time, and in this embodiment, the time interval between the first time and the second time is 48~72 hours; however, the present invention is not limited to such time only, and the length of time can be shortened or increased depending upon the needs.

As shown in Step S13, the computation processing unit 2 performs computation process based on the second electric signal to generate a second concentration value corresponding to the AGEs. Since its method is similar to that of Step S5, the details thereof are omitted hereafter.

As shown in Step S15, the computation processing unit 2 generates a concentration change amount based on a difference between the first concentration value and the second concentration value, in order to utilize the concentration change amount to determine whether the concentration value of the AGEs is increasing or decreasing. In this embodiment, it is expected that after the intervention of the music program, the concentration value of the AGEs can be gradually reduced to a certain level.

As shown in Step S17, the computation processing unit 2 further compares the concentration change amount with the predefined concentration change amount. In this embodiment, the predefined concentration change amount is 30 mg/dL; however, the present invention is not limited to such value only. Accordingly, when the concentration change amount is not less than 30 mg/dL, a second matching result is generated, and it means that after the music program is provided, the concentration value of the AGEs decreases as expected. On the contrary, when the concentration change amount is less than 30 mg/dL, a third matching result is generated, and it means that after the music program is provided, the concentration value of the AGEs fails to decrease as expected.

Furthermore, the second matching result refers to the computation processing unit 2 drives the music unit 3 to correspondingly play one of the plurality of first music menus 31 according to the second concentration value, meaning that the music program of the first music menus 31 is provided correspondingly according to the decreased concentration value of the AGEs. Similarly, the second matching result may further include a second time information, allowing the music unit 3 to correspondingly play one of the first music menus 31 according to the second time information. Since its method is similar to that of Step S7, details thereof are omitted hereafter. In addition, when the second concentration value falls within the third predefined concentration range, at this time, the computation processing unit 2 drives the music unit 3 to play the first music menus 31 and the third music menu 33 in turns.

Moreover, the third matching result refers to the computation processing unit 2 driving the music unit 3 to play one of the plurality of first music menus 31 correspondingly according to the second concentration value. Similarly, the third matching result may further include a third time information, allowing the music unit 3 to correspondingly play one of the plurality of first music menus 31 according to the third time information. In addition, the music unit 3 is also driven to play the second music menu 32 according to the concentration change amount during a corresponding time interval. In addition, the time interval comprises a first time interval, a second time interval and a third time interval.

When the concentration change amount is less than 10 mg/dL, it corresponds to the first time interval. In this embodiment, the first time interval is 15~30 minutes. During the playing of the first music menus 31, the music of the second music menu 32 is played once every 15~30 minutes; however, the present invention is not limited to such configuration only.

When the concentration change amount is not less than 10 mg/dL but less than 20 mg/dL, it corresponds to the second time interval. In this embodiment, the second time interval is 30~45 minutes. During the playing of the first music menus 31, the music of the second music menu 32 is played once every 30~45 minutes; however, the present invention is not limited to such configuration only.

When the concentration change amount is not less than 20 mg/dL but less than 30 mg/dL, it corresponds to the third time interval. In this embodiment, the third time interval is 45~60 minutes. During the playing of the first music menus 31, the music of the second music menu 32 is played once every 45~60 minutes; however, the present invention is not limited to such configuration only.

In other words, when the treatment effect under the music program with the use of the first music menus is poor, the second music menu 32 is additionally used to provide stimulation, such that the norepinephrine of the patient can be increased in a short time, thereby enhancing the treatment effect of the music program. Accordingly, when the concentration change amount is lower, it requires the intervention of greater stimulation, in order to prevent the reduction of the treatment effect under the same course of treatment due to fatigue of the patient.

In view of the above, for the music matching application system with use of AGEs and method thereof of the present invention, it is able to use the sensor unit of the wearable device to detect the parameter value of a skin surface, followed by using the computation processing unit to perform computation process based on the parameter value in order to obtain an electric signal to convert into a corresponding concentration value of the AGEs. Next, the music unit is driven to correspondingly play one of the first music menus according to the concentration change amount, and it is also able to play a second music menu according to a concentration change amount corresponding to a time interval. Consequently, it is able to achieve the effect of significant improvement of the music program, and patient is not likely to feel fatigue, such that objectives of the present invention can be effectively achieved.

However, it shall be noted that the aforementioned embodiments refer to the preferred embodiments of the present invention only such that they shall not be used to limit the scope of the present invention, i.e. All simple equivalent changes and modifications made based on the claims and the content of the description of the present invention shall be considered to be within the scope of the present invention.

What is claimed is:

1. A music matching application method with use of Advanced Glycation End-Products (AGEs), comprising the steps of:
   providing a wearable device comprising a wearable piece and a sensor unit; the sensor unit arranged on the wearable piece; the wearable piece being worn by a skin surface of a human body; and
   the sensor unit detecting a first parameter value of the skin surface during a first time;
   a computation processing unit receiving the first parameter value and performing computation process based on the first parameter value to obtain a first electric signal;
   providing a music unit connected in signal with the computation processing unit and comprising a plurality of first music menus and a second music menu;
   the computation processing unit performing computation process based on the first electric signal to generate a first concentration value corresponding to AGEs;
   the computation processing unit performing computation process based on the first concentration value to generate a first matching result;
   the computation processing unit driving the sensor unit to detect a second parameter value of the skin surface during a second time;
   the computation processing unit receiving the second parameter value and performing computation process based on the second parameter value to obtain a second electric signal;
   the computation processing unit performing computation process based on the second electric signal to generate a second concentration value corresponding to the AGEs;
   the computation processing unit generating a concentration change amount based on a difference between the first concentration value and the second concentration value; and
   when the concentration change amount being not less than a predefined concentration change amount, generating a second matching result, and when the concentration change amount being less than the predefined concentration change amount, generating a third matching result; wherein the first matching result refers to the computation processing unit driving the music unit to play one of the plurality of first music menus corresponding according to the first concentration value; wherein the second matching result refers to the computation processing unit driving the music unit to play one of the plurality of first music menus corresponding according to the second concentration value; and wherein the third matching result refers to the computation processing unit driving the music unit to play one of the plurality of first music menus corresponding according to the second concentration value, and driving the music unit to play the second music menu according to the concentration change amount during a corresponding time interval.

2. The music matching application method with use of Advanced Glycation End-Products (AGEs) according to claim 1, wherein the sensor unit is a capacitive bio-sensor, an optical bio-sensor or an ultrasonic bio-sensor.

3. The music matching application method with use of Advanced Glycation End-Products (AGEs) according to claim 1, wherein the predefined concentration value comprises a first predefined concentration range, a second predefined concentration range and a third predefined concentration range; the first predefined concentration range is less than 300 mg/dL; the second predefined concentration range is between 300 mg/dL and 600 mg/dL; and the third predefined concentration range is greater than 600 mg/dL.

4. The music matching application method with use of Advanced Glycation End-Products (AGEs) according to claim 3, wherein the music unit comprises a third music menu; when the first concentration value falls within the third predefined concentration range, the computation processing unit drives the music unit to play the third music menu.

5. The music matching application method with use of Advanced Glycation End-Products (AGEs) according to claim 1, wherein the first matching result comprises a first time information, allowing the music unit to play one of the plurality of first music menus correspondingly according to the first time information.

6. The music matching application method with use of Advanced Glycation End-Products (AGEs) according to claim 1, wherein the second matching result comprises a second time information, allowing the music unit to play one of the plurality of first music menus correspondingly according to the second time information.

7. The music matching application method with use of Advanced Glycation End-Products (AGEs) according to claim 1, wherein the third matching result comprises a third time information, allowing the music unit to play one of the plurality of first music menus corresponding according to the third time information.

8. The music matching application method with use of Advanced Glycation End-Products (AGEs) according to claim 1, wherein the predefined concentration change amount is between 10 mg/dL and 30 mg/dL.

9. The music matching application method with use of Advanced Glycation End-Products (AGEs) according to claim 1, wherein the time interval comprises a first time interval, a second time interval and a third time interval.

10. The music matching application method with use of Advanced Glycation End-Products (AGEs) according to claim 9, wherein when the concentration change amount is less than 10 mg/dL, it corresponds to the first time interval; when the concentration change amount is not less than 10 mg/dL but less than 20 mg/dL, it corresponds to the second time interval; and when the concentration change amount is not less than 20 mg/dL but less than 30 mg/dL, it corresponds to the third time interval.

* * * * *